US012629455B2

(12) United States Patent
Park et al.

(10) Patent No.: US 12,629,455 B2
(45) Date of Patent: May 19, 2026

(54) HYALURONIC ACID-BASED HYDROGEL USING PEPTIDE CROSSLINKING AGENT, AND METHOD FOR PRODUCING SAME

(71) Applicant: CHAMEDITECH Co., Ltd., Daejeon (KR)

(72) Inventors: Kyeong-Yong Park, Daejeon (KR); Jun-Goo Kang, Cheongju-si (KR); Seoung Jin Lee, Daejeon (KR); Sok Jin Kim, Gunpo-si (KR)

(73) Assignee: CHAMEDITECH CO., LTD., Daejeon (KR)

( * ) Notice: Subject to any disclaimer, the term of this patent is extended or adjusted under 35 U.S.C. 154(b) by 691 days.

(21) Appl. No.: 17/922,825

(22) PCT Filed: Mar. 16, 2021

(86) PCT No.: PCT/KR2021/003260
§ 371 (c)(1),
(2) Date: Nov. 2, 2022

(87) PCT Pub. No.: WO2021/235662
PCT Pub. Date: Nov. 25, 2021

(65) Prior Publication Data

US 2023/0158211 A1 May 25, 2023

(30) Foreign Application Priority Data

May 19, 2020 (KR) ........................ 10-2020-0059991

(51) Int. Cl.
*A61L 27/52* (2006.01)
*A61F 2/00* (2006.01)
(Continued)

(52) U.S. Cl.
CPC ............... *A61L 27/52* (2013.01); *A61L 27/20* (2013.01); *C08J 3/075* (2013.01); *C08K 5/20* (2013.01);
(Continued)

(58) Field of Classification Search
None
See application file for complete search history.

(56) References Cited

U.S. PATENT DOCUMENTS

2009/0263447 A1* 10/2009 Asius .................... A61L 31/145 536/29.1

FOREIGN PATENT DOCUMENTS

| | | |
|---|---|---|
| JP | 2020-503278 | 1/2020 |
| KR | 10-2009-0109084 | 10/2009 |

(Continued)

OTHER PUBLICATIONS

KIPO, PCT Search Report & Written Opinion of PCT/KR2021/003260 dated Jul. 26, 2021.

*Primary Examiner* — Kyung S Chang
(74) *Attorney, Agent, or Firm* — LEX IP MEISTER, PLLC

(57) ABSTRACT

The present invention relates to a hyaluronic acid-based hydrogel which is a hyaluronic acid-peptide crosslinked body crosslinked using a peptide crosslinking agent. More specifically, the present invention relates to a hyaluronic acid-based hydrogel and a method for producing same, wherein a crosslinked body having novel physical properties is obtained using a relatively small amount of a crosslinking agent that forms peptide bonds, unlike conventional cross-linking agents, and the hyaluronic acid-based hydrogel has the advantages of: being safe and having few side effects; the
(Continued)

A HA Hydrogel Manufacturing Process
Using Peptide Crosslinking Agent physical properties of a filler being adjustable according to the amount of peptide crosslinking; and having a high elasticity ratio.

8 Claims, 1 Drawing Sheet

(51) Int. Cl.

| | |
|---|---|
| ***A61K 8/04*** | (2006.01) |
| ***A61K 8/64*** | (2006.01) |
| ***A61K 8/73*** | (2006.01) |
| ***A61L 27/20*** | (2006.01) |
| ***C08J 3/075*** | (2006.01) |
| ***C08K 5/20*** | (2006.01) |
| ***C08L 5/08*** | (2006.01) |

(52) U.S. Cl.
CPC ............... *C08L 5/08* (2013.01); *A61F 2/0059* (2013.01); *A61L 2400/06* (2013.01); *A61L 2430/34* (2013.01)

(56) References Cited

FOREIGN PATENT DOCUMENTS

| | | |
|---|---|---|
| KR | 10-2015-0040966 | 4/2015 |
| KR | 10-2016-0110723 | 9/2016 |
| KR | 10-2020-0035807 | 4/2020 |
| KR | 10-2225971 | 3/2021 |

* cited by examiner

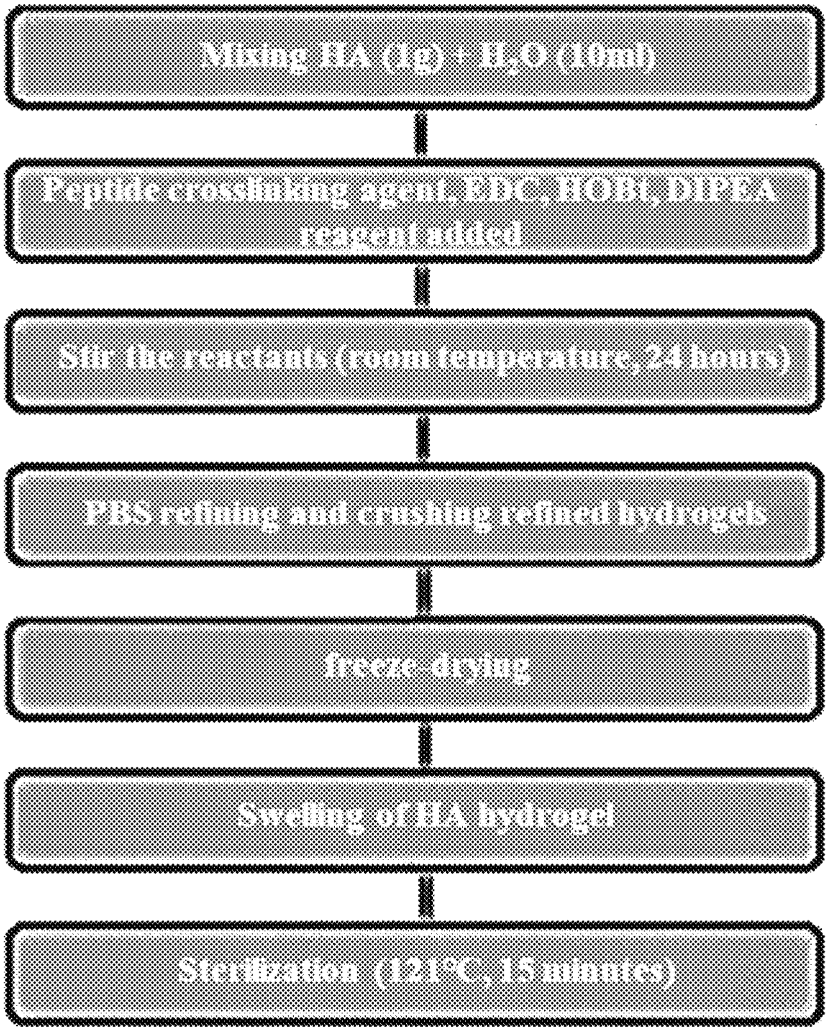
A HA Hydrogel Manufacturing Process
Using Peptide Crosslinking Agent

HYALURONIC ACID-BASED HYDROGEL USING PEPTIDE CROSSLINKING AGENT, AND METHOD FOR PRODUCING SAME

TECHNICAL FIELD

The present invention relates to a hyaluronic acid-based hydrogel and a method for manufacturing thereof, and more specifically, it relates to a cross-linked body of hyaluronic acid-peptide obtained by cross-linking hyaluronic acid using a peptide cross-linking agent and a method for manufacturing thereof.

BACKGROUND ART

Hyaluronic acid (HA) is a biocompatible material, a major raw material for dermal fillers, but has a very short half-life (>1 day). However, the hyaluronic acid-cross-linking binding process using a cross-linking agent can increase the decomposition period of hyaluronic acid and physical properties such as viscoelasticity. Among these cross-linking agents, BDDE (1,4-Butanediol diglycidyl ether) compounds are the most used, and recently, cross-linking agents such as DVS (Divinyl sulfone), PEGDGE (Poly (ethylene glycol) diglycidyl ether) and the like have been used. The cross-linking binding reaction with hyaluronic acid is achieved as the primary alcohol group of hyaluronic acid and the epoxide group of BDDE are reacted to form an ether bond in a basic aqueous solution as Reaction formula 1 below.

[Reaction Formula 1]

Hyaluronic acid-cross-linking binding method using BDDE cross-linking agent

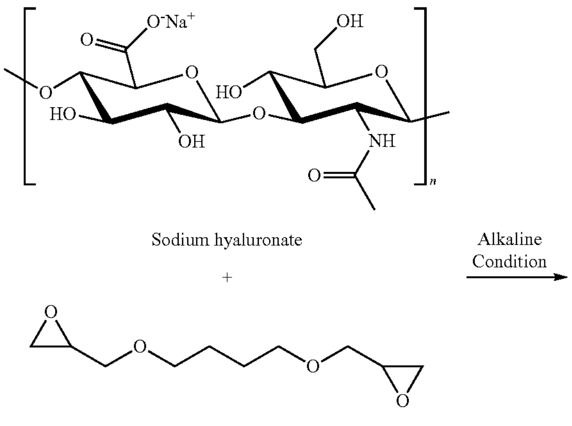

Sodium hyaluronate

+

BDDE

-continued

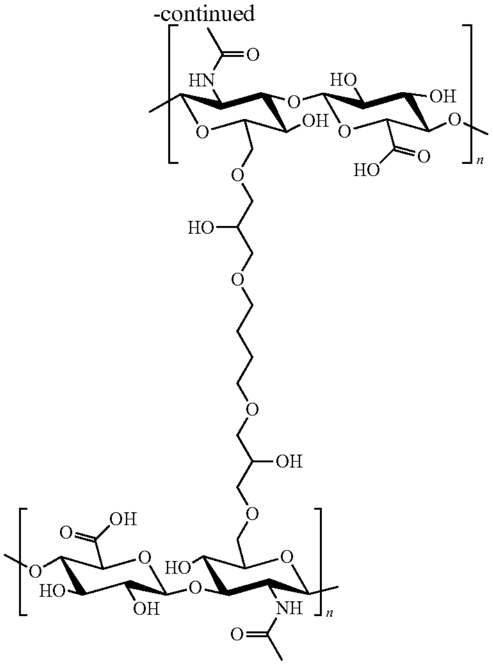

In general, an amount of about 5~10 mol % of the BDDE cross-linking agent is reacted with hyaluronic acid, to form a hyaluronic acid-cross-linking binding filler. Then, in the process of purifying the used BDDE cross-linking agent, a lot of time and money are incurred, and after injecting the filler with the unremoved BDDE compound into a body, adverse reaction and side effects occur.

DISCLOSURE

Technical Problem

Under the above background, the present inventors have conducted extensive research to proceed with hyaluronic acid-cross-linking reaction using a safe peptide cross-linking agent, instead of the commonly widely used BDDE cross-linking agent. As a result, they have confirmed that when hyaluronic acid is cross-linked using a peptide-based cross-linking agent, a carboxylic acid group of hyaluronic acid and an amine group of the peptide cross-linking agent are reacted to form an amide bond, and this reaction is a method significantly different from the conventional binding method, and can obtain a cross-linked filler with new physical properties with a relatively small amount of cross-linking agent, thereby completing the present invention.

[Reaction Formula 2]

Hyaluronic acid-cross-linking binding method using a peptide cross-linking agent according to the present invention

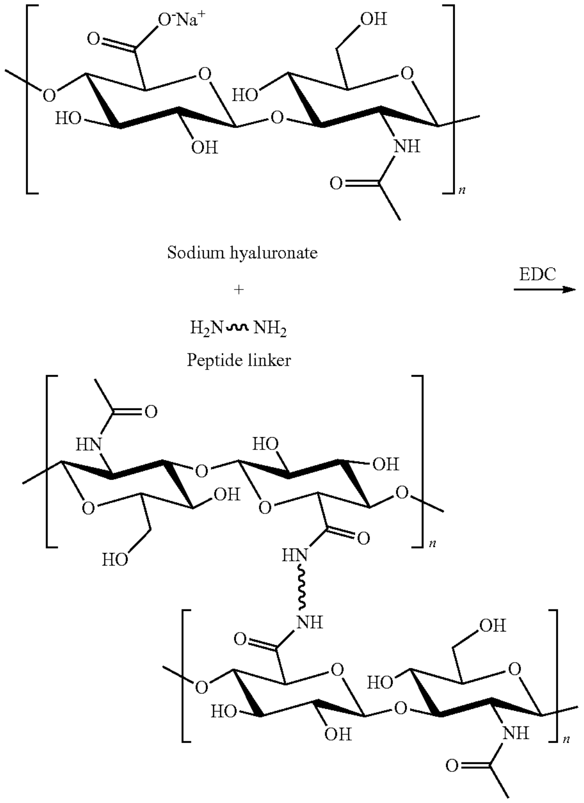

Therefore, an object of the present invention is to provide a hyaluronic acid-based hydrogel, which is a hyaluronic acid-peptide cross-linked body which cross-links hyaluronic acid or a salt thereof using a peptide cross-linking agent, and therefore, has few side effects, is safe, has a characteristic of a high elastic ratio, and is obtained by the peptide cross-linking agent and this cross-linking process. This hyaluronic acid-based hydrogel is useful as a filler for injection into a human body.

Another object of the present invention is to provide a method for manufacturing the peptide cross-linking agent and hyaluronic acid-based hydrogel.

Technical Solution

In order to solve the above problems, the present invention provides a hyaluronic acid-based hydrogel comprising a peptide cross-linking agent and hyaluronic acid or a salt thereof, the peptide cross-linking agent and a method for manufacturing of the hyaluronic acid-based hydrogel and the peptide cross-linking agent. The hyaluronic acid-based hydrogel is a hyaluronic acid-peptide cross-linked body in which hyaluronic acid is cross-linked using the peptide cross-linking agent.

Hyaluronic acid is an anionic glycosaminoglycan distributed in epithelial and neural tissues. It is a major component of the extracellular matrix and is necessary for wound treatment because it plays an important role of wound regeneration, inflammatory response and angiogenesis. It is a substance that performs various functions in relation to human skin by playing an important role in re-epithelialization in which the skin surface that has been removed from the epidermis re-proliferates even in normal epidermis. In the present invention, it is a hyaluronic acid-peptide cross-linked body formed by using this hyaluronic acid as a monomer and using the peptide cross-linking agent, that is, a hyaluronic acid-based hydrogel. The salt of hyaluronic acid may be for example, one or more selected from the group consisting of sodium hyaluronate, calcium hyaluronate, magnesium hyaluronate, zinc hyaluronate, cobalt hyaluronate and tetrabutylammonium hyaluronate, but not limited thereto.

The hyaluronic acid or salt may have a weight average molecular weight (Mw) of 200 to 5,000 kDa, 500 to 4,000 kDa, 600 to 3,000 kDa, or 700 to 1,000 kDa. Using hyaluronic acid or a salt thereof in the weight average molecular weight, the reactivity with a cross-linking agent and the easiness of hydrogel manufacturing can be enhanced, and the physical properties of the manufactured hydrogel can be improved.

The hyaluronic acid-based hydrogel according to the present invention comprises a peptide cross-linking agent and hyaluronic acid, and a carboxylic acid group of hyaluronic acid and an amine group of the peptide cross-linking agent are reacted to form an amide bond through cross-linking reaction, and preferably, it may have the structure of Chemical formula 1 below.

[Chemical formula 1]

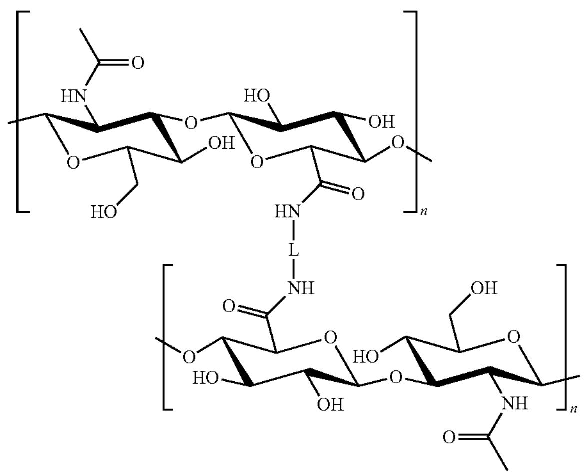

In the formula, n is an integer of 500 to 1,400, and L comprises 3 kinds to 10 kinds of amino acids. The L is a structure formed by the peptide cross-linking agent, and may comprise 3 kinds to 9 kinds, 3 kinds to 8 kinds, 3 kinds to 7 kinds, 3 kinds to 6 kinds or 3 kinds or 5 kinds of amino acids. For the amino acid, any amino acid capable of forming a peptide can be used without limitation, but for example, it may be an amino acid selected from the group consisting of glutamic acid (Glu), aspartic acid (Asp), glutamine (Gln), asparagine (Asn), histidine (His), lysine (Lys), arginine (Arg), serine (Ser), cysteine (Cys), beta alanine (β-Ala), alanine (Ala), glycine (Gly), leucine (Leu), isoleucine (Ile), valine (Val), threonine (Thr), methionine (Met), proline (Pro), phenylalanine (Phe), tyrosine (Tyr) and tryptophan (Trp). In addition, the L preferably comprises one or more of lysine.

The hyaluronic acid comprised in the hyaluronic acid-based hydrogel according to the present invention may be hyaluronic acid having a molecular weight of 200,000 to 300,000 Da, 200,000 to 400,000 Da, 200,000 to 500,000 Da, 200,000 to 600,000 Da, 200,000 to 700,000 Da, 200,000 to 800,000 Da, 200,000 to 900,000 Da, 200,000 to 1,000,000 Da, 200,000 to 1,100,000 Da, 200,000 to 1,200,000 Da, 300,000 to 400,000 Da, 300,000 to 500,000 Da, 300,000 to 600,000 Da, 300,000 to 700,000 Da, 300,000 to 800,000 Da, 300,000 to 900,000 Da, 300,000 to 1,000,000 Da, 300,000 to 1,100,000 Da, 300,000 to 1,200,000 Da, 400,000 to 500,000 Da, 400,000 to 600,000 Da, 400,000 to 700,000 Da, 400,000 to 800,000 Da, 400,000 to 900,000 Da, 400,000 to 1,000,000 Da, 400,000 to 1,100,000 Da, 400,000 to 1,200,000 Da, 500,000 to 600,000 Da, 500,000 to 700,000 Da, 500,000 to 800,000 Da, 500,000 to 900,000 Da, 500,000 to 1,000,000 Da, 500,000 to 1,100,000 Da, 500,000 to 1,200,000 Da, 600,000 to 700,000 Da, 600,000 to 800,000 Da, 600,000 to 900,000 Da, 600,000 to 1,000,000 Da, 600,000 to 1,100,000 Da, 600,000 to 1,200,000 Da, 700,000 to 800,000 Da, 700,000 to 900,000 Da, 700,000 to 1,000,000 Da, 700,000 to 1,100,000 Da, 700,000 to 1,200,000 Da, 800,000 to 900,000 Da, 800,000 to 1,000,000 Da, 800,000 to 1,100,000 Da, 800,000 to 1,200,000 Da, 900,000 to 1,000,000 Da, 900,000 to 1,100,000 Da, 900,000 to 1,200,000 Da, 1,000,000 to 1,100,000 Da, 1,000,000 to 1,200,000 Da, or 1,100,000 to 1,200,000 Da.

"Cross-linking" of the term "cross-linking agent" means binding reaction in which one polymer chain is linked to the same or different chain. Such a connection may have a form of a covalent bond or an ionic bond, and may have an effect that as the number of cross-linking increases, solubility and thermoplasticity decrease, but mechanical strength increases and the elasticity of the polymer compound increases. As a cross-linking agent used for cross-linking hyaluronic acid, conventionally, BDDE (1,4-Butanediol diglycidyl ether), DVS (Divinyl sulfone), PEGDGE (Poly (ethylene glycol) diglycidyl ether), 1,6-hexanediol diglycidyl ether, propylene glycol diglycidyl ether, poly(propylene glycol) diglycidyl ether, poly(tetramethylene glycol) diglycidyl ether, and the like have been used, but the hyaluronic acid-based hydrogel of the present invention is characterized of being cross-linked using a new peptide cross-linking agent to be described below, not the cross-linking agent described above. In case of cross-linked hyaluronic acid, it forms a matrix, and this matrix may have a network of cross-linked or non-cross-linked polysaccharides in the form of a solution or gel.

In the hyaluronic acid-based hydrogel according to the present invention, the peptide cross-linking agent forms an amide bond by reacting a carboxylic acid group of hyaluronic acid and an amine group of the peptide cross-linking agent, differently from BDDE conventionally widely used for cross-linking of hyaluronic acid, which forms an ether bond by reacting a primary alcohol group of hyaluronic acid and an epoxide group of BDDE are reacted.

Preferably, the peptide cross-linking agent may comprise 3 kinds to 10 kinds, 3 kinds to 9 kinds, 3 kinds to 8 kinds, 3 kinds to 7 kinds, 3 kinds to 6 kinds, or 3 kinds to 5 kinds of amino acids. For the amino acid, any amino acid capable of forming a peptide may be used without limitation, but for example, it may be an amino acid selected from the group consisting of glutamic acid (Glu), aspartic acid (Asp), glutamine (Gln), asparagine (Asn), histidine (His), lysine (Lys), arginine (Arg), serine (Ser), cysteine (Cys), beta alanine (β-Ala), alanine (Ala), glycine (Gly), leucine (Leu), isoleucine (Ile), valine (Val), threonine (Thr), methionine (Met), proline (Pro), phenylalanine (Phe), tyrosine (Tyr) and tryptophan (Trp). In addition, the peptide cross-linking agent preferably comprises one or more of lysine.

As a preferable aspect, the peptide cross-linking agent according to the present invention may have any one structure of Chemical formulas 2 to 4 below.

$X_1—X^2—X_3$ [Chemical formula 2]

$Y_1—Y_2—Y_3—Y_4$ [Chemical formula 3]

$Z_1—Z_2—Z_3—Z_4—Z_5$ [Chemical formula 4]

In the formula, $X_3$, $Y_4$ and $Z_5$ may be each independently lysine (Lys), and $X_1$, $X_2$, $Y_1$, $Y_2$, $Y_3$, $Z_1$, $Z_2$, $Z_3$ and Z4 may be each independently selected from the group consisting of glutamine (Gln), asparagine (Asn), serine (Ser), cysteine (Cys), beta alanine (β-Ala), alanine (Ala), glycine (Gly), leucine (Leu), isoleucine (Ile), valine (Val), threonine (Thr), methionine (Met), proline (Pro), phenylalanine (Phe), tyrosine (Tyr) and tryptophan (Trp), but not limited thereto.

In the Chemical formulas 2 to 4, lysine of $X_3$, $Y_4$ and $Z_5$ may comprise an amide group ($—CONH_2$) instead of a carboxylic group (—COOH).

As can be confirmed in the Chemical formulas 2 to 4, the peptide cross-linking agent according to the present invention proceeds cross-linking by forming an amide bond with a carboxylic acid group of hyaluronic acid.

In addition, the present invention relates to a method for manufacturing of a peptide cross-linking agent comprising synthesizing a peptide using 1 to 10 kinds of amino acids selected from the group consisting of glutamic acid (Glu), aspartic acid (Asp), glutamine (Gln), asparagine (Asn), histidine (His), lysine (Lys), arginine (Arg), serine (Ser), cysteine (Cys), beta alanine (β-Ala), alanine (Ala), glycine (Gly), leucine (Leu), isoleucine (Ile), valine (Val), threonine (Thr), methionine (Met), proline (Pro), phenylalanine (Phe), tyrosine (Tyr) and tryptophan (Trp).

For the synthesis method of a peptide, conventionally known synthesis methods of a peptide (for example, solution phase synthesis method or solid phase synthesis method) may be used without limitation, but preferably, a solid phase peptide synthesis method (SPPS) that is easy to separate and purify and can be automated may be used. In the present invention, when a peptide is synthesized according to the solid phase peptide synthesis method, a peptide cross-linking agent may be manufactured using an amino acid in which the N-terminus of the amino acid is protected with a Fmoc (fluorenylmethyloxycarbonyl) protective group.

As one specific aspect, the method for manufacturing of the peptide cross-linking agent may comprise the following steps:

i) binding a side chain or C-terminus of the first amino acid to a polymer supporter resin;

ii) removing a protective group at the N-terminus of the first amino acid;

iii) binding amino acids in order using a coupling agent to synthesize a peptide; and iv) removing the resin and protective group from the peptide synthesized in the iii).

The polymer supporter resin used in the step i) may be selected from polystyrene, polyamide, glass or silica. In one example according to the present invention, Rink Amide MBHA resin was used.

In the method of manufacturing according to the present invention, the amine terminus and side chain of the amino acid used for manufacturing of a peptide may be protected with a protective group selected from Boc (tert-butoxycarbonyl), Fmoc (9-fluorenylmethoxycarbonyl), Cbz (benzyloxycarbonyl), tBu (tert-butyl), StBu (tert-butylthio), Trt (triphenylmethyl; trityl), Acm (acetamidomethyl) or Tacm (trimethylacetamido-methyl). Preferably, it may be protected with a Fmoc (9-fluorenylmethoxycarbonyl) protective group.

Preferably, one or more of the amino acids composing the peptide in the step iii) are lysine.

In addition, the coupling agent used in the step iii) may be one kind selected from the group consisting of NHS (N-hydroxysulfosuccinimide), HOBt (1-hydroxybenzotriazole), HOOBt (3,4-dihydro-3-hydroxy-4-oxo-1,2,3-benzotriazine), HOAt (1-hydroxy-7-azabenzotriazole), Sul-NHS (Sulfo-N-hydroxysulfosuccinimide) and TBTU [O-(1H-benzotriazole-1-yl)-N,N,N',N'-tetramethyluronium tetrafluoroborate] and salts thereof or a mixture thereof, and preferably, it may be HOBt (1-hydroxybenzotriazole), but not limited thereto.

As a reaction solvent of the present invention, dichloromethane, dimethylformamide, dimethylacetamide, N-methylpyrrolidinone or a mixed solvent thereof commonly used in chemical reaction is used as the reaction solvent, and preferably, it may be dichloromethane, dimethylformamide solvent and a mixed solvent. The reaction temperature of the reactions disclosed in the present invention has no limitation, but it is in a range of preferably, 0° C. to 70° C., more preferably, 20° C. to 40° C. The reaction time is in a range of 10 minutes to 48 hours, and preferably, it is in a range of 1 hour to 24 hours, considering the reactivity of each reactant and productivity of products after the reaction. However, when the reaction has not progressed as much as desired, the reaction yield may be increased by further performing the same reaction 2 times to 5 times.

Furthermore, in the present invention, the method for manufacturing of the peptide cross-linking agent may comprise a step of confirming whether a reaction occurs when amino acids are bound using the coupling agent. In the example according to the present invention, the reaction was confirmed by Kaiser test. The step of confirming this coupling reaction may be performed preferably after the step iii) in which the reaction is achieved.

Moreover, in the step ii), the protective group of the N-terminus, preferably, Fmoc group may be removed using a DMF solution (specifically, DMF solution diluted with 20% piperidine).

In the step iv), the resin and protective group may be separated by adding a weak acidic cleavage solution such as TFA (trifluoroacetic acid) aqueous solution, TIS (triisopropylsilane) aqueous solution, TFA:TIS mixed aqueous solution, or DCM (dichloromethane), or the like. In one example according to the present invention, it could be removed using cleavage cocktail [TFA:$H_2O$=95:5 (v/v)] solution.

As other one aspect, the present invention relates to a method for manufacturing of a hyaluronic acid-based hydrogel, which is a hyaluronic acid-peptide cross-linked body, comprising the following steps:

i) manufacturing a peptide using 1 kind to 10 kinds of amino acids selected from the group consisting of glutamic acid (Glu), aspartic acid (Asp), glutamine (Gln), asparagine (Asn), histidine (His), lysine (Lys), arginine (Arg), serine (Ser), cysteine (Cys), beta alanine (β-Ala), alanine (Ala), glycine (Gly), leucine (Leu), isoleucine (Ile), valine (Val), threonine (Thr), methionine (Met), proline (Pro), phenylalanine (Phe), tyrosine (Tyr) and tryptophan (Trp); and ii) manufacturing a hyaluronic acid cross-linked body comprising a peptide cross-linking agent by adding the peptide cross-linking agent synthesized in the step i), a coupling agent, an auxiliary coupling agent, and a base after adding distilled water to hyaluronic acid.

The step i) of the method for manufacturing a hyaluronic acid-based hydrogel may be performed by a solid phase peptide synthesis method.

The peptide cross-linking agent used in the step ii) of the method for manufacturing a hyaluronic acid-based hydrogel is 0.01-0.1 equivalent compared to a disaccharide (D-glucuronic acid and N-acetylglucosamine) which is a component of hyaluronic acid.

The coupling agent in the step ii) may be one kind selected from the group consisting of EDC (1-ethyl-3-(3-dimethylaminopropyl) carbodiimide hydrochloride), ETC [1-ethyl-3-(3-dimethylaminopropyl) carbodiimide], CMC [1-cyclohexyl-3-(2-morpholinoethyl) carbodiimide] and salts thereof or a mixture thereof, and preferably, it may be EDC (1-ethyl-3-(3-dimethylaminopropyl) carbodiimide hydrochloride), but not limited thereto.

The auxiliary coupling agent in the step ii) may be one kind selected from the group consisting of NHS (N-hydroxysulfosuccinimide), HOBt(1-hydroxybenzotriazole), HOOBt (3,4-dihydro-3-hydroxy-4-oxo-1,2,3-benzotriazine), HOAt (1-hydroxy-7-azabenzotriazole), Sul-NHS (Sulfo-N-hydroxysulfosuccinimide), TBTU [O-(1H-benzotriazole-1-yl)-N,N,N',N'-tetramethyluronium tetrafluoroborate] and salts thereof or a mixture thereof, and preferably, it may be HOBt (1-hydroxybenzotriazole), but not limited thereto.

In the step ii), the base may be one kind selected from the group consisting of DIPEA [N,N-Diisopropylethylamine], TEA (triethylamine), TDA-1 {Tris[2-(2-methoxyethoxy) ethyl]amine} and salts thereof or a mixture thereof, and preferably, it may be DIPEA [N,N-Diisopropylethylamine], but not limited thereto.

The step ii) of the method for manufacturing may be performed at a temperature of 20° C. to 40° C. for 2 hours, 4 hours, 8 hours, 16 hours or 24 hours, and preferably, the reaction may be carried out at a room temperature for 24 hours.

In the method for manufacturing a hyaluronic acid-based hydrogel, the following steps may be further comprised:

iii) washing the cross-linked body manufactured in the step ii) with phosphate-buffered saline (PBS) solution to remove unreacted substances;

iv) pulverizing the cross-linked body washed in the step iii); and v) sterilizing the cross-linked body pulverized in the step iv), after the step ii).

Washing with phosphate-buffered saline solution in the step iii) may be performed several times.

In the step iv), the cross-linked body may be pulverized in a particle size of about 100~500 μm, and in the step v), sterilizing may be performed at a temperature of 121° C. to 135° C. for 8 minutes to 20 minutes, and preferably, sterilizing may be performed at 121° C. for 15 minutes.

In one specific example, physical properties of the hyaluronic acid-based hydrogel according to the present invention were analyzed using a rotational rheometer. The rheometer analysis was measured within a frequency range of 0.1~1 Hz, and after adding the sample to Plate-Plate, a normal force value was measured when it was rotated at a shear rate of $10^{-1}$ for 0.1 second and the upper plate was dropped at a rate of 0.1 mm/s. In addition, for the syringe ability of the manufactured cross-linked body, an injection force value was measured by analyzing at a rate of 12 mm/min, after equipping a syringe comprising 1 ml of the cross-linked body in a syringe ability test machine. By physical property analysis, the elasticity, viscosity, tan 6, complex viscosity and injection force may be measured.

Regarding the physical properties measured with the rheometer, "elasticity" refers to a property that if a force is added when a force is applied to a substance or object, the shape changes, but returns to its original state when the force is removed. Such elasticity is expressed as G' (elastic modulus, storage modulus), and the unit is expressed as Pa. The higher the elasticity value, the harder the gel and the greater the ability to resist deformation, so it has an important meaning in terms of the wrinkle improvement effect of a filler.

The term "viscosity" refers to resistance of fluids that appears when the shape changes or a property that parts attached to each other do not fall off, and an object that flows well has a smaller viscosity value. This viscosity is expressed as G" (viscous modulus, loss modulus), and the unit is expressed as Pa.

The term "Tan δ" is a numerical value indicating whether a substance is closer to a solid or a liquid, and is expressed as G"/G'. The lower the Tan δ, it has a solid property, and on the contrary, the higher the Tan δ, it has a liquid property.

The term "complex viscosity" is a method of expressing viscosity including G' and G" values, and it is dependent on the value of the frequency (ω), and the value is obtained by the following formula. This complex viscosity is expressed as |η*| (complex viscosity), and the unit is expressed as mPa·s.

$$|\eta^*|=\sqrt{(G'/\omega)_2+(G''/\omega)^2}$$

In addition, the term "injection force" refers to a value of a force when a syringe needle (27 G) is connected to a syringe to which a cross-linked filler is added, and a syringe pusher is pushed at a rate of 12.0 mm/min, and the unit of this injection force is expressed as N.

For evaluation of the degradation ability of the hyaluronic acid-peptide cross-linked body according to the present invention, as same as viscosity, the complex viscosity over time of samples was confirmed with a rheometer equipment, thereby confirming the degradation ability of the cross-linked body.

For evaluation of the absorption ability of the hyaluronic acid-peptide cross-linked body according to the present invention, the cross-linked body and phosphate buffer solution are added to a falcon tube, and then are stirred. Such a mixture is left at 37° C. for 72 hours, and then Coomassie Brilliant Blue solution is added, to confirm the layer separation and color difference. Using the layer separation as a boundary, the volume of the hyaluronic acid-peptide complex hydrogel sinking in the lower layer was confirmed, and it was applied to Equation 1 below to confirm the absorption ability.

Absorption solvent amount=swelled volume÷weight of specimen (ml/g) [Equation 1]

The hyaluronic acid-based hydrogel according to the present invention uses a peptide cross-linking agent, and therefore, it has high stability and elasticity, so it can be used as a composition for injection into a body, and can be very usefully used for a cosmetic or therapeutic purpose. Accordingly, the present invention provides a composition for injection into a body comprising the hyaluronic acid-cross-linked body. The composition for injection into a body can be used in various fields, for example, as a filler or implant for facial plastic surgery or tissue repair, an anti-adhesion agent, or an orthopedic adjuvant. In addition to this, it can be used for various uses even as a dental filler, a cell supporter or a drug delivery system, or the like. As a specific example of these uses, it can be used as a filler for repairing wrinkles, fine wrinkles, glabellar wrinkles, acetabular labrum wrinkles, chin wrinkles, marionette wrinkles, mouth drills, perioral wrinkles, fine wrinkles around eyes, skin dents, scars, wounds or skin depressions, temples, subdermal support of eyebrows, cheekbone and cheek fat pads, or treatment of tear sulcus, noses, lips, cheeks, perioral regions, suborbital regions, facial asymmetry, lower jaw lines and chins.

As one aspect, the present invention provides a method for improvement of wrinkles or a method for tissue repair or volume increase comprising administering the hyaluronic acid-based hydrogel. The method for injection of a composition for injection into a body comprising the hyaluronic acid-based hydrogel and the like is known well in the art, and through this method for injection, various wrinkles illustrated above can be improved, and tissue repair or a tissue volume can be increased. Specifically, the tissue may be soft tissue such as lip, nose, hip, cheek or breast. The hyaluronic acid hydrogel may be administered in a suitable administration form for this use, and it may be preferably, an injection formulation, more preferably, a pre-filled syringe.

Advantageous Effects

The peptide cross-linking filler of the present invention has fewer side effects than the previous BDDE cross-linking agent filler, is safe, and has a characteristic of controlling physical properties of the filler according to the amount of peptide cross-linking. In addition, it is useful because in terms of physical properties, it has a characteristic of a higher elastic ratio than conventional fillers, so it can satisfy the diversify possibility of filter products and needs of new consumers. In addition, it can be applied to eye drop and knee arthritis fields, which are products of which safety is emphasized.

BRIEF DESCRIPTION OF THE DRAWINGS

FIG. 1 is a drawing of schematizing one embodiment of the process of manufacturing the hyaluronic acid-based hydrogel using a peptide cross-linking agent according to the present invention.

MODE FOR INVENTION

Hereinafter, the present invention will be described in detail by examples. However, the following examples illustrates the present invention only, but the present invention is not limited by the following examples.

EXAMPLE 1

Synthesis of Ala-Leu-Lys-NH2, which is the Peptide Cross-Linking Agent According to the Present Invention For manufacturing the peptide cross-linking agent according to the present invention, the process of [Reaction formula 3] was conducted.

[Reaction Formula 3]

Synthesis of tri-peptide, which is the peptide cross-linking agent of the present invention

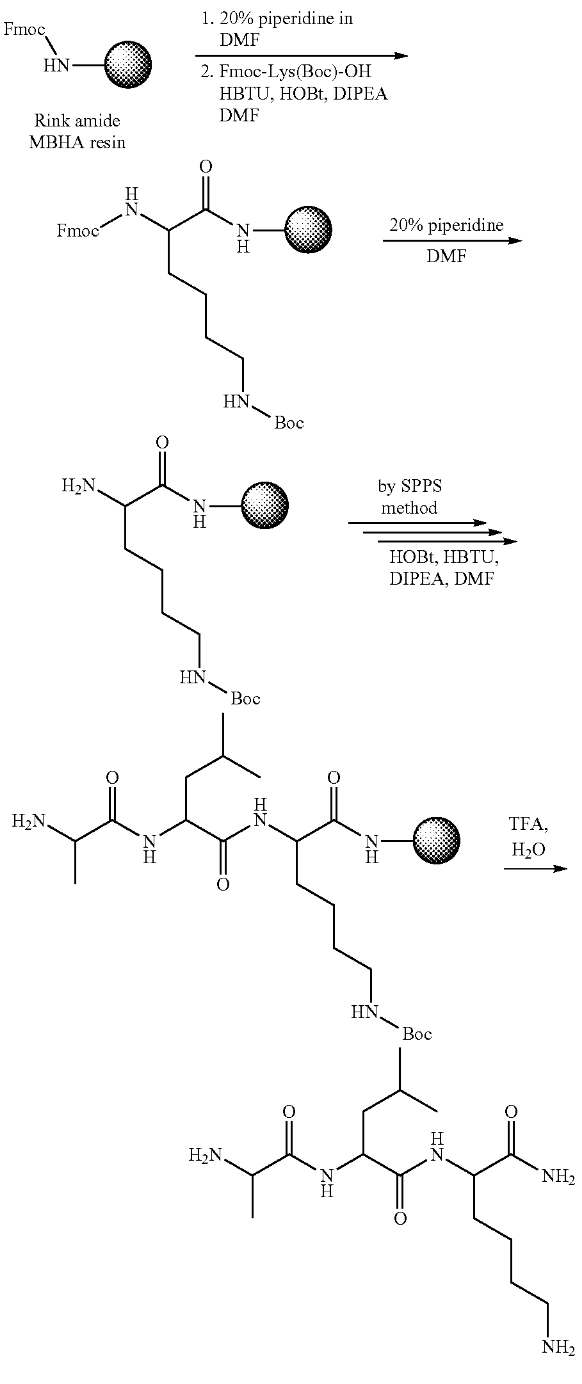

1) Rink amide MBHA resin (0.502 mmol/g) 996 mg (500 umol) purchased from Novabiochem was weighed and placed in a reaction container. The resin was swelled for 5 minutes using DMF (N,N-Dimethylformamide) and the solvent was removed under reduced pressure. After removing Fmoc (9-Fluorenylmethoxycarbonyl) using DMF solution diluted with 20% piperidine in the reaction container, amino acids (3 equivalents) and HOBt (1-hydroxybenzotriazole) (3 equivalents), HBTU (N,N,N,N-Tetramethyl-O-(1H-benzotriazol-1-yl)uranium hexafluorophosphate) (3 equivalents), DIPEA (N,N-Diisopropylethylamine) (6 equivalents) were added, and the reaction was carried out for 4 hours.

2) After reaction, solvent removal and washing of the resin were performed, and then Fmoc (9-Fluorenylmethoxycarbonyl) removal reaction was carried out using DMF solution diluted with 20% piperidine (5 min×2 times).

3) The coupling reaction of the amino acid and resin was performed using amino acids (3 equivalents)/HOBt (3 equivalents)/HBTU (3 equivalents)/DIPEA (6 equivalents) reagents for 4 hours.

4) The coupling reaction was confirmed using a qualitative method called kaiser test (E. Kaiser et al., Anal. *Biochem.* 1970, 34, 595), and then, the Kaiser solution consists of three kinds. [a. ninhydrin (5 g)+ethanol (100 ml); b. phenol (80 g)+ethanol (20 ml); c. pyridine (98 ml)+0.002 M aq. KCN (2 ml)] After completing the coupling reaction, the resin was washed, and then 2-3 drops of the three kinds of the Kaiser test solution were added, and then heat was applied at 120° C. for 3 minutes. When the unreacted part remained, the color of the resin showed a blue light, and when it was completely reacted, there was no change in the color of the resin.

5) After synthesizing a desired peptide derivative by repeating 2)-4) processes, the resin and protective group removal was carried out using cleavage cocktail [TFA:H2O=95:5 (v/v)] solution.

EXAMPLE 2

Manufacturing of Cross-Linked Body of Hyaluronic Acid-Peptide According to the Present Invention For manufacturing of the hyaluronic acid-based hydrogel according to the present invention, the following process was conducted.

The reaction was carried out at a room temperature for 24 hours by adding 10 ml distilled water to 1 g hyaluronic acid, making the tri-peptide synthesized in Example 1 to be 0.012 equivalents (Example 1a), 0.014 equivalents (Example 1b), 0.016 equivalents (Example 1c), and 0.018 equivalents (Example 1d), and adding EDC [1-Ethyl-3-(3-dimethylaminopropyl) carbodiimide; 0.01~0.1 equivalents], HOBt [1-Hydroxybenzotriazole; 0.01~0.1 equivalents], DIPEA [N,N-Diisopropylethylamine; 0.02~0.2 equivalents) reagents. The manufactured cross-linked body was washed with phosphate-buffered saline (PBS) solution several times to remove unreacted substances, and the washed cross-linked body was pulverized to adjust to a particle size of about 100~500 μm, and then it was sterilized at 121° C. for 15 minutes.

EXAMPLE 3

Analysis of Physical Properties of Cross-Linked Body of Hyaluronic Acid-Peptide Manufactured by the Present Invention For analysis of physical properties of manufactured Example 2, the concentration of the cross-linked body was manufactured as 20 mg/PBS 1 ml, and then it was analyzed using a rotational rheometer. Then, the rheometer analysis was measured within a frequency range of 0.02 Hz, and after adding the sample to Plate-Plate, a normal force value was measured when it was rotated at a shear rate of $10^{-1}$ for 0.1 second and the upper plate was dropped at a rate of 0.1 mm/s.

<Analysis Condition>

(1) Test equipment: MCR Rheometer (Anton Paar)
(2) Frequency: 1~10 Hz
(3) Temperature: 25±0.01° C.
(4) Strain: 1%
(5) Minimum torque oscillation: 10 nN*m
(6) Maximum torque: 150 nN*m
(7) Torque resolution: 0.1 nN*m
(8) Measuring geometry: 25 mm plate
(9) Measuring Gap: 1.0 mm In addition, for the syringe ability (injection force) of the manufactured cross-linked body, the injection force value was measured by analyzing it at a rate of 12 mm/min, after equipping a syringe comprising 1 ml of the cross-linked body in a syringe ability test machine.

Through Table 1, it could be seen that the complex viscosity varied depending on the amount of the peptide to be cross-linked. Since the complex viscosity increased as the amount of the peptide increased, it could be seen that the complex viscosity could be controlled by adjusting the peptide amount during cross-linking.

TABLE 1

| Cross-linked sample | Elasticity (G') | Viscosity (G") | Tan δ | Complex viscosity (mPa · s) | Injection force (N) |
|---|---|---|---|---|---|
| Example 1a | 101 | 36 | 0.35 | 852,000 | 15 |
| Example 1b | 169 | 38 | 0.22 | 1,380,000 | 23 |
| Example 1c | 310 | 53 | 0.17 | 2,500,000 | 28 |
| Example 1d | 444 | 108 | 0.24 | 3,640,000 | 31 |

EXAMPLE 4

Evaluation of Decomposition Ability of Cross-Linked Body of Hyaluronic Acid-Peptide Manufactured by the Present Invention In order to evaluate the decomposition ability of manufactured Example 2, the weight of 0.6 g of the hyaluronic acid-peptide cross-linked body in a micro 2 ml tube was measured, and then hyaluronidase solution (33 mg/mL) (MP biomedicals) of 6 μL was added in each tube. Samples of the mixture cross-linked body was collected at 37° C. by time, and the complex viscosity of the samples was confirmed with a rheometer equipment, thereby confirming the decomposition ability of the cross-linked body.

Through Table 2, the complex viscosity change over time was confirmed, thereby the decomposition ability of the cross-linked body. As a result of confirming the degree of decomposition in vitro, it could be confirmed that Example 1d had a viscosity of 3,640,000 at 0 hour, but had a viscosity of 1,740,000 after 4 hours, and therefore, it was decomposed about 52.2% after 4 hours.

TABLE 2

| Cross-linked | Complex viscosity of cross-linked body over time (mPa · s) | | | |
|---|---|---|---|---|
| sample | 0 hour | 1 hours | 2 hours | 4 hours |
| Example 1a | 852,000 | 321,000 | 186,000 | 142,000 |
| Example 1b | 1,380,000 | 749,000 | 471,000 | 313,000 |
| Example 1c | 2,500,000 | 1,350,000 | 1190,000 | 678,000 |
| Example 1d | 3,640,000 | 2,680,000 | 2,330,000 | 1,740,000 |

EXAMPLE 5

Evaluation of Absorption Ability of Cross-Linked Body of Hyaluronic Acid-Peptide Manufactured by the Present Invention In order to evaluate the absorption ability of manufactured Example 2, the hyaluronic acid-peptide cross-linked body (Example 1a-1d) 0.6 g and phosphate buffer solution 10 ml were added to a falcon 50 ml tube, and then stirred for 5 minutes. Such a mixture was left at 37° C. for 72 hours, and then Coomassie Brilliant Blue solution 100 μl was added to confirm the layer separation and color difference. Using the layer separation as a boundary, the volume of the hyaluronic acid-peptide complex hydrogel sinking in the lower layer was confirmed, and it was applied to Equation 1 below to confirm the absorption ability.

Absorption solvent amount=swelled volume÷weight of specimen (ml/g) [Equation 1]

As can be confirmed in Table 3, general fillers had a swelled volume between 5~8, but the swelled volume of the hyaluronic acid-peptide cross-linked body (cross-linked sample) according to the present invention showed a value between 2~3. This means that the peptide filter has a characteristic that does not swell well.

TABLE 3

| Cross-linked sample | Swelled volume (ml) | Test liquid weight (g) | Absorption solvent amount (ml/g) |
|---|---|---|---|
| Example 1a | 3.0 | 0.6 | 5.00 |
| Example 1b | 3.0 | 0.6 | 5.00 |
| Example 1c | 2.5 | 0.6 | 4.17 |
| Example 1d | 2.1 | 0.6 | 3.50 |

The invention claimed is:

1. A hyaluronic acid-based hydrogel comprising a peptide cross-linking agent comprising 3-5 of amino acids and a hyaluronic acid or a salt thereof, wherein the peptide cross-linking agent has any one structure of the following Chemical formulas 2 to 4, $X_1—X^2—X_3—NH_2$ [Chemical formula 2]

$Y_1—Y_2—Y_3—Y_4—NH_2$ [Chemical formula 3]

$Z_1—Z_2—Z_3—Z_4—Z_5—NH_2$ [Chemical formula 4]

in the formula, $X_3$, $Y_4$ and $Z_5$ are each independently lysine (Lys), $X_1$, $X_2$, $Y_1$, $Y_2$, $Y_3$, $Z_1$, $Z_2$, $Z_3$ and $Z_4$ are each independently selected from the group consisting of glutamine (Gln), asparagine (Asn), serine (Ser), cysteine (Cys), beta alanine β-Ala), alanine (Ala), glycine (Gly), leucine (Leu), isoleucine (Ile), valine (Val), threonine (Thr), methionine (Met), proline (Pro), phenylalanine (Phe), tyrosine (Tyr) and tryptophan (Trp), in the Chemical formulas 2 to 4, lysine of $X_3$, $Y_4$ and $Z_5$ comprises an amide group (—$CONH_2$) instead of a carboxyl group (—COOH), and wherein the $NH_2$ group of the Chemical formulas 2 to 4 is the amino group of the amide group (—$CONH_2$).

2. The hyaluronic acid-based hydrogel according to claim 1, having the structure of the following Chemical formula 1:

[Chemical formula 1]

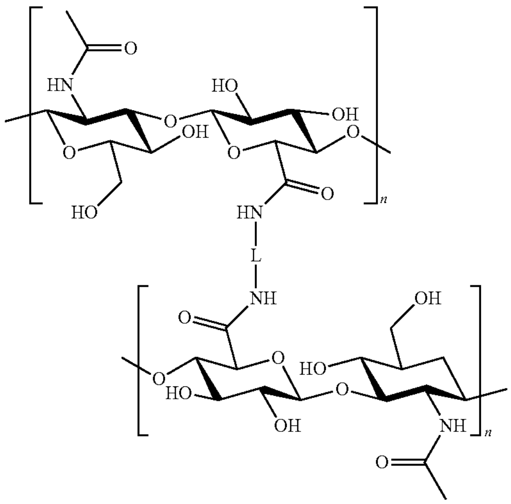

and in the formula, n is an integer of 500 to 1,400, and L comprises 3-5 of amino acids.

3. The hyaluronic acid-based hydrogel according to claim 1, wherein the hyaluronic acid has a molecular weight of 200,000~1,200,000 Da.

4. A composition for injection into a body, comprising the hyaluronic acid-based hydrogel according to claim 1.

5. An implant for tissue repair comprising the composition for injection into a body according to claim 4.

6. A filler for repair of wrinkles, fine wrinkles, wound or skin depression comprising the composition for injection into a body according to claim 4.

7. A method for improvement of wrinkles, comprising injecting the hyaluronic acid-based hydrogel according to claim 1 into a body.

8. A method for tissue repair or volume increase, comprising injecting the hyaluronic acid-based hydrogel according to claim 1 into a body.

* * * * *